(12) United States Patent
Seelich et al.

(10) Patent No.: US 6,579,537 B2
(45) Date of Patent: *Jun. 17, 2003

(54) METHOD FOR PRODUCING FIBRONECTIN AND FIBRINOGEN COMPOSITIONS USING A POLYALKYLENE GLYCOL AND GLYCINE OR β-ALANINE

(75) Inventors: Thomas Seelich, Vienna (AT); Ralf Broermann, Vienna (AT)

(73) Assignee: Baxter Aktiengesellschaft, Vienna (AT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/502,029

(22) Filed: Feb. 10, 2000

(65) Prior Publication Data

US 2002/0172718 A1 Nov. 21, 2002

(30) Foreign Application Priority Data

Feb. 12, 1999 (AT) .................................. 206/99

(51) Int. Cl.[7] ........................ A61K 35/16; A61K 38/48; C12N 9/48
(52) U.S. Cl. ...................... 424/530; 435/212; 435/183; 435/214; 424/94.64
(58) Field of Search ................. 435/212, 183, 435/214; 424/530, 94.64

(56) References Cited

U.S. PATENT DOCUMENTS

| | | | |
|---|---|---|---|
| 4,453,939 A | * | 6/1984 | Zimmerman et al. ....... 604/368 |
| 4,640,834 A | | 2/1987 | Eibl et al. |
| 4,650,678 A | | 3/1987 | Fuhge et al. |
| 4,909,251 A | | 3/1990 | Seelich |
| 5,288,853 A | * | 2/1994 | Bhattacharva et al. ...... 530/383 |
| 5,474,770 A | | 12/1995 | Broly et al. |
| 5,578,326 A | * | 11/1996 | Weis-Fogh .................. 424/529 |
| 5,610,147 A | | 3/1997 | Seelich |
| 5,614,405 A | | 3/1997 | Eibl et al. |
| 5,639,730 A | | 6/1997 | Eibl et al. |
| 5,733,885 A | | 3/1998 | Eibl et al. |
| 5,770,199 A | | 6/1998 | Eibl et al. |
| 5,864,016 A | | 1/1999 | Eibl et al. |
| 5,962,405 A | | 10/1999 | Seelich |
| 6,056,970 A | * | 5/2000 | Greenwalt et al. .......... 424/426 |

FOREIGN PATENT DOCUMENTS

| | | | |
|---|---|---|---|
| EP | 0 131 740 A2 | | 1/1985 |
| JP | 1-99565 | * | 4/1989 |
| JP | 4-347162 | * | 12/1992 |
| WO | WO 92/13495 | | 8/1992 |
| WO | WO 94/20524 | | 9/1994 |
| WO | WO 95/23167 | | 8/1995 |
| WO | WO 96/35437 | | 11/1996 |
| WO | WO 99/15209 | | 4/1999 |

OTHER PUBLICATIONS

Blombäck, B. et al., *Purification of Human and Bovine Fibrinogen*, Arkiv För Kemi, 10:9, pp. 415–443 (1956).
Hao, Y.L., et al., *Fractional Precipitation of Proteins with Polyethylene Glycol, Methods of Plasma Protein Fractionation*, Academic Press, Ed. J.M. Curling, pp. 57–74 (1980).
Kistler, P., et al., *Ethanol Precipitation, Methods of Plasma Protein Fractionation*, Academic Press, Ed. J.M. Curling, pp. 3–15 (1980).
Redl, H., et al., *Med. Welt*, No. 22, pp. 3–10 (1985). (Translation attached, 19 pages).
Steinbuch, M., *Protein Fractionation by Ammonium Sulphate, Rivanol® and Caprylic Acid Precipitation, Methods of Plasma Protein Fractionation*, Academic Press, Ed. J.M. Curling, pp. 33–36 (1980).

* cited by examiner

*Primary Examiner*—Michael V. Meller
(74) *Attorney, Agent, or Firm*—Annette S. Parent; Janice Guthrie

(57) ABSTRACT

A method of producing a pharmaceutical preparation comprising fibronectin and fibrinogen is disclosed. The method involves admixing into a starting solution of fibrinogen and fibronectin, in a single step, a precipitating composition comprising a polyalkylene glycol and at least one of glycine and β-alanine which forms a precipitate. Next, the precipitate is collected and a pharmaceutical preparation is prepared from the precipitate. The pharmaceutical preparation has a fibronectin:fibrinogen ratio from about 0.02 to about 0.2.

18 Claims, 2 Drawing Sheets

METHOD FOR PRODUCING FIBRONECTIN AND FIBRINOGEN COMPOSITIONS USING A POLYALKYLENE GLYCOL AND GLYCINE OR β-ALANINE

CROSS REFERENCES TO RELATED APPLICATIONS

The present application claims priority to Austrian application number A 206/99, filed Feb. 12, 1999.

STATEMENT REGARDING FEDERALLY SPONSORED RESEARCH OR DEVELOPMENT

Not applicable

BACKGROUND OF THE INVENTION

The invention relates to a method for producing protein compositions comprising fibronectin and fibrinogen and, optionally, further ingredients as well as to protein compositions obtainable according to this method.

Tissue adhesives based on fibrinogen ("fibrin adhesives") have been known for a long time. They serve for a seamless or suture-supporting connection of human or animal tissues or organ parts, for sealing wounds, haemostasis and assisting wound healing.

Their mode of action is based on an imitation of the final phase of blood coagulation.

By the action of thrombin, (soluble) fibrinogen at first is converted into fibrin monomers which aggregate spontaneously and form a sticky mass, a so-called fibrin clot. Simultaneously, factor XIII (F XIII) present is activated by thrombin in the presence of calcium ions to factor XIIIa. By the latter, the aggregated fibrin monomers and also fibronectin possibly present are cross-linked to a high polymer by new peptide bonds forming. By this cross-linking reaction, the strength of the clot formed is substantially increased. Generally, the clot adheres well to wound and tissue surfaces, which i.a. leads to the adhesive and haemostatic effect.

Therefore, fibrin adhesives frequently are used as two-component adhesives which comprise the fibrinogen component together with a thrombin solution which additionally contains calcium ions.

A particular advantage of a fibrin adhesive consists in that the latter does not remain at its site of application as a foreign body, but is completely resorbed just as in natural wound healing, and is replaced by newly formed tissue. Various cells, such as, e.g., macrophages and, subsequently, fibroblasts migrate into the clot, lyse and resorb the clot material and form new tissue.

Although the complicated procedures of wound healing so far by no means have become completely clear, it is considered to be certain that the presence of fibronectin in the clot is of crucial importance for the growing in of cells and thus for wound healing.

A fibrin clot of optimum composition threrefore should also comprise a content of fibronectin in addition to its main component, fibrinogen.

Although the mode of action of fibrin adhesives substantially corresponds to the natural processes of blood coagulation, for a sufficient efficacy (adhesive strength, haemostatic effect), a substantially higher concentration of the active components (in particular, of fibrinogen) is necessary than is present in blood, the fibrinogen concentration of human blood amounting to approximately 2.5–3 mg/ml.

It has been reported that by means of PEG precipitation a fibrinogen solution could be obtained with which a satisfactory adhesive strength could be attained already at fibrinogen concentrations of below 30 mg/ml in an artificial test system (WO 92/13495), yet with this, for many purposes of tissue adhesion a high density of the fibrin network (and the latter is substantially only attainable by high fibrinogen concentrations in the tissue adhesive) cannot be ensured, To ensure an optimum efficacy, therefore, the fibrinogen content in a fibrin adhesive should be at least 70 mg/ml. The production of such concentrated ready-to-use fibrinogen or fibrin adhesive solutions, respectively, does, however, involve some difficulties:

Since the ready-to-use solutions are not storage-stable over longer periods of time, they have to be prepared upon demand either by reconstitution from lyophilized preparations or by thawing of liquid-deep frozen solutions.

Because of the relatively poor solubility of fibrinogen and the simultaneously required high fibrinogen concentration in an effective fibrin adhesive, in general this is still more cumbersome and time-consuming than desired by users thereof, despite diverse proposals for improvements. It is understandable that particularly in the field of emergency surgery, a particularly rapid and simple availability of a fibrin adhesive is required.

Moreover, concentrated fibrin adhesive solutions generally are highly viscous due to their high fibrinogen concentrations. A relatively low viscosity, however, is desirable not only for easier handling, but also for specific modes of application of a fibrin adhesive, e.g. when applying it by means of spray devices (such as, e.g., Duploject® with the associated spray set), or by means of a catheter.

Both requirements, i.e. rapid availability and low viscosity of the ready-to-use fibrin adhesive solutions, are even more difficult to meet if preparation thereof (dissolution or thawing, respectively) is to be effected without further auxiliary means, such as heating and/or stirring equipment, at room temperature, and if the fibrin adhesive preparations additionally contain high-molecular substances, in particular fibronectin. For also fibronectin—particularly in combination with fibrinogen—is relatively difficult to dissolve and generally leads to an even poorer solubility and an increased viscosity of fibrin adhesives.

Methods for producing fibrinogen-containing preparations which can be used as tissue adhesives comprise i.a. their production from cryoprecipitate, optionally with further washing and precipitation steps with ethanol, ammonium sulphate, polyethylene glycol, glycine or β-alanine, and their production from plasma within the scope of the known plasma fractionation methods, respectively (cf., e.g., "Methods of plasma protein fractionation", 1980, ed.: Curling, Academic Press, pp. 3–15, 33–36 and 57–74, or Blomback B. and M., "Purification of human and bovine fibrinogen", Arkiv Kemi 10, 1959, p. 415 f.).

In the prior art, also various suggestions have been made to reduce the viscosity of highly concentrated fibrinogen solutions. Thus, e.g., the addition of solubilizers, such as substances containing urea or guanidine residue, e.g. arginine (cf. DE 3203775-A1), or the addition of unphysiologically high salt concentrations has been known. However, it has been shown that such tissue adhesives have cytotoxic and proliferation-inhibiting properties, respectively (Redl et al., Med. Welt 36, 1985, pp. 769–776)

According to EP 0 804 933, the addition of substances improving the solubility of fibrinogen has been suggested. Such substances are, e.g., vitamins, aromatic compounds, such as compounds derived from benzene or phenol, or those derived from heterocyclic compounds, such as piperidine, pyridine or pyrimidine.

Thus, it is an object of the present invention to overcome the drawbacks of known preparations, and to further improve the known preparations, respectively, and to provide protein compositions comprising a high fibrinogen content and an easily adjustable ratio of fibrinogen to fibronectin as well as, optionally, further ingredients, which are, e.g., suitable for an improved preparation of ready-to-use tissue adhesives, while particularly maintaining properties, such as a good cell compatibility, or the formation of a physiological fibrin structure after mixing with a thrombin solution. At the same time, also the viscosity properties of such protein compositions or pharmaceutical preparations are to be improved.

A further object of the present invention is to provide a simplified and more rapid method of producing such protein compositions. In particular, it shall also be possible to easily carry out the method on an industrial scale.

SUMMARY OF THE INVENTION

According to the invention, these objects are achieved by a method for producing protein compositions which comprise fibrinogen and fibronectin, which method is characterized in that a starting solution comprising fibrinogen and fibronectin is treated with a precipitating composition which comprises two different components that modify the solubility of fibrinogen and/or fibronectin, so that in a single-step precipitation a fibrinogen and fibronectin containing precipitate is formed, and the formed precipitate optionally is further treated by methods known per se. This method is characterized in that an efficient and protein-preserving preparation giving high yields can be produced with the precipitating composition by a single-step precipitation.

Following the single-step precipitation, the precipitate obtained may be further processed by methods known per se, preferably into a pharmaceutical preparation, in particular a tissue adhesive (fibrin adhesive).

By a solubility-modifying component, a substance is understood which has a precipitating effect or a solubility-improving effect on at least one of the proteins, fibrinogen or fibronectin, under the given other conditions, such as temperature, pH, ionic strength, etc.

Quite surprisingly, according to the invention it has been found that using two solubility-modifying components which are different (from each other) in cooperation allows for a recovery of fibrinogen and fibronectin in the precipitate in high yields, wherein the single-step precipitation of the invention quite amazingly has been found to be substantially less protein-damaging than the individual precipitation of the respective substances.

Moreover, it has also been shown that a composition precipitated according to the invention and comprising fibrinogen and fibronectin has enormously improved properties also with a view to its practical application, in particular as regards its viscosity and reconstitution, whereby an easier application of these preparations is made possible.

As the starting materials for preparing the starting solution, in principle all those can be used which so far have been used or are possible, respectively, in the prior art for preparing such protein compositions.

As the starting material, preferably, plasma, in particular human plasma, or a fibrinogen and fibronectin-comprising plasma fraction, preferably a fraction derived from cryoprecipitate, is used for preparing the starting solution or is used directly as starting solution, respectively.

Other fibrinogen and fibronectin-comprising starting materials or starting solutions, respectively, such as, e.g., cell culture supernatants, may, however, also be employed according to the invention.

The solubility-modifying components are chosen such that in a single-step precipitation a precipitate is formed which contains fibrinogen and fibronectin in a desired and pre-determined ratio of amounts.

According to the invention, the components contained in the precipitating composition are chosen such that, under the given conditions, they differ from each other in terms of their solubility-modifying, i.e. solubility-improving or precipitating, action on fibrinogen and fibronectin, respectively. One component may, for instance, have a precipitating effect substantially on merely one of the two proteins, i.e. on fibrinogen or on fibronectin.

It is, however, also possible that one of the components has a precipitating action on both proteins, whereas the other component has a precipitating action on merely one of the two proteins, or even increases the solubility of the other protein, respectively, i.e. does not act as a precipitating agent but as a solubilizer.

In particular, the solubility-modifying component is a substance selected from the group of alcohol, in particular alcohol having up to four carbon atoms, inorganic salt, organic salt, polyol, in particular polyalkylene glycol, polyether and amino acid. Also ethers, ketones and cyclic, heterocyclic or polycyclic organic compounds may be used. As the solubility-modifying components, particularly ethanol, polyethylene glycol, ammonium or alkali salts, respectively, such as ammonium sulfate or alkali sulfate, or the amino acids glycine and ($\beta$-) alanine are preferably used.

Among the organic polymers, there are particularly the linear polymers, in particular those having an average molecular a weight approximately between 200 and 20,000, e.g. polyalkylene glycols. Polyethylene glycol has proven particularly suitable. These non-toxic, water-soluble synthetic polymers, in particular those having a molecular weight of from 400 to 10,000, preferably around 4,000, are preferably used in the precipitation because of their preserving effect on fibrinogen and fibronectin. In addition to the particularly gentle and preserving effect of the components to be used in the precipitating composition, also their safety as regards their use on humans is taken into consideration when selecting them.

As a pair of components usable according to the invention, for instance, polyethylene glycol (PEG), in particular PEG 4000 which has a precipitating action both on fibrinogen and on fibronectin, and, as the second component, glycine is usable, which in the presence of a further component, e.g. polyethylene glycol, surprisingly not only preferably precipitates fibrinogen as compared to fibronectin, but even acts as a solubilizer for fibronectin. Glycine in a concentration range of more than 0.6 M, in which so far glycine has only been known as a protein precipitating agent, has a particularly good, fibronectin-solubility increasing effect.

Of course, the present invention is not limited to combinations of PEG and glycine, since the average skilled artisan will easily be able to find also other components or component pairs, respectively, suitable according to the invention, by means of simple systematic tests.

To carry out the method of the invention, the skilled artisan may, e.g. find suitable components or component pairs, respectively, according to the following test scheme. Under defined conditions, such as temperature, pH, ionic strength etc. and under stirring, aliquots of a starting solution prepared by common methods are admixed with precipitating compositions containing a first solubility-modifying component, e.g. an amino acid, and a second component different therefrom, e.g. PEG 4000, ethanol or ammonium sulfate. Precipitation series are carried out in which the concentration of one of the components always is kept constant, and the other one is varied. The precipitates formed are centrifuged off, and the total protein content as well as the relative contents of fibrinogen (Fbg), fibronectin (Fn) and albumin (Alb) are determined, e.g. by means of SDS PAGE of the non-reduced and reduced samples, staining with Coomassie Blue and densitometric evaluation.

Those components which lead to the desired fibrinogen and fibronectin-containing protein composition are then chosen for the precipitating composition according to the invention. Optimization of the respective component system will be effected by means of parameters easy to check, such as yield, relative content of fibrinogen and fibronectin, and viscosity, respectively, of the obtained preparation at a pre-determined fibrinogen-content (e.g. 70 or 100 mg of fibrinogen per ml).

In a preferred embodiment, the precipitating composition comprises polyalkylene glycol which is admixed to the starting solution, in particular to a final concentration of from 1 to 12% w/v, preferably from 4 to 8% w/v.

In a further preferred embodiment, the precipitating composition comprises one or more amino acids admixed to the starting solution, in particular to a final concentration of from 0.5 to 3 M, preferably 0.75 to 2 M, in particular 0.75 to 1.5 M.

In another preferred embodiment, an organic or inorganic salt, e.g. ammonium sulfate, is contained at a concentration of up to 20% w/v, preferably between 2 to 20% w/v, most preferred between 5 to 15% w/v.

The precipitating composition preferably is admixed in liquid form.

Also other ingredients of the starting material can be precipitated by means of the precipitating composition, such as in particular factor XIII. Also the ability of the solubility-modifying composition for co-precipitating such further substances may influence the final choice of the individual components in the precipitating composition.

According to a preferred embodiment it is attempted to keep the plasminogen in the precipitated protein composition or in the pharmaceutical preparation, respectively, rather low. Accordingly, preferably a precipitating composition is used in which plasminogen largely remains in the supernatant, which means that in the precipitate obtained, plasminogen is depleted relative to fibrinogen and/or fibronectin, as compared to the starting material.

According to a further preferred embodiment, further ingredients, in particular fibrinolysis inhibitors, factor XIII, antibiotics, growth factors, pain-alleviating substances, anti-inflammatory agents or mixtures thereof may be added to the protein composition. Such additions are possible before, during, and also after the precipitation step and preferably are effected after the precipitation step.

In the course of further processing, in particular in the final formulation, the protein composition according to the invention or the pharmaceutical preparation according to the invention preferably is deep-frozen or lyophilized, particularly if an improved storage stability is to be achieved. The ready-to-use pharmaceutical preparation according to the present invention preferably is provided in liquid form.

In particular, the method according to the invention has the advantage that well-defined protein compositions are obtainable directly in a simple manner, whereas hitherto used methods of protein fractionation, in particular of plasma fractionation, always have aimed at obtaining individual proteins as pure as possible and, optionally, at mixing them together again afterwards to give the desired mixture.

By the simplicity and brevity of the method according to the invention, also the danger of microbial contamination and the formation of pyrogens during production are minimized. Moreover, sensitive plasma proteins, such as, e.g., fibrinogen or fibronectin, are preserved and largely protected from denaturing, and this is probably why the preparations according to the invention have improved properties.

For surprisingly it has been shown that the protein compositions or pharmaceutical preparations, respectively, obtainable by the single-step combination precipitation of the invention, at similarly high fibrinogen concentrations have an approximately 25%, preferably even 30%, most preferred 40%, lower viscosity than comparable preparations, e.g. fibrin adhesives obtained by the classical production methods, in particular by precipitation with one agent only.

By comparable preparations, preparations are understood which have similar contents of fibrinogen, fibronectin and, optionally, further ingredients, and a comparable degree of purity, which exhibit a similarly good cell compatibility and which form clots of physiological fibrin structure after having been mixed with a thrombin solution.

In a particularly preferred embodiment, the protein composition and the ready-to-use pharmaceutical preparation, respectively, substantially do not contain any substances improving the solubility of the fibrinogen, and no such substances are admixed, respectively.

Surprisingly it has been shown that liquid compositions according to the invention have a markedly lower viscosity as compared to comparable known preparations, whereby particularly handling and use of fibrin adhesives is facilitated. Particularly at room temperature, the lyophilized compositions according to the invention can be reconstituted more easily and more rapidly than comparable preparations.

Particularly when carrying out the method of the invention on a large technical scale which—and this is a further advantage of the present invention—can be applied on a large scale very efficiently and in a cost-saving manner, it is preferred to admix the precipitating composition in liquid form. This may be a solution or a suspension.

It has also proven suitable that the precipitate obtained after the single-step precipitation is washed at least once with a washing buffer. In addition to a suitable buffer system, the washing buffer preferably contains tranexamic acid, lysine, $\epsilon$-aminocaproic acid, detergents, or mixtures of these substances. Also fibrinolysis inhibitors or protease inhibitors, respectively, of plasmatic, animal or plant origin, or inhibitors produced by genetical engineering or synthetically, respectively, may be contained. Such substances may be admixed separately, or they may already be contained in the starting material.

A preferred protease inhibitor is, e.g., aprotinin, in particular aprotinin prepared by genetical engineering. A further preferred fibrinolysis inhibitor is tranexamic acid (trans-4-(aminomethyl)-cyclohexane carboxylic acid, t-AMCHA).

The protein precipitate obtained may be used as such, or it may be further processed to a further protein composition or to a pharmaceutical preparation, respectively, by methods known per se. Such methods for processing include, e.g., diverse purification steps, such as, e.g., treatment (washing) with a buffer solution in the cold, or formulation as a pharmaceutical preparation, respectively.

In particular, such final compositions or preparations, respectively, of the invention are suitable for tissue adhesion, haemostasis, and aiding or promoting wound healing.

Plasma which preferably is used as the starting material for the present invention, preferably is sufficiently preselected, e.g. according to the method of WO 96/35437, so that virus contamination can nearly be excluded. Preferably, only such a starting material is used which has been checked for an absence of pathogens, in particular viruses and/or prions.

In a further preferred embodiment, at least one step for inactivating or depleting possibly present pathogens is provided.

To inactivate pathogens, preferably a tenside and/or heat treatment (dry or vapor treatment) is carried out, e.g. a heat treatment in the solid state, in particular a vapor treatment according to EP-0 159 311, or EP-0 519 901, or EP-0 674 531.

Further treatments for pathogen inactivation also comprise treatment with chemical or chemical/physical methods, e.g. with chaotropic substances according to W094/13329, DE 4434538 or EP-0131740 (solvent), or photoinactivation.

Also the depletion by means of filtration, in particular ultrafiltration, preferably in the presence of virus-binding agents, such as, e.g. Aerosil, is a preferred method for depleting viruses within the scope of the present invention.

According to the invention, inactivation by means of a heat treatment, a solvent treatment, a detergent treatment, or a combination (simultaneous or sequential) of these treatments, as well as, optionally, a filtration, are particularly preferred.

Inactivation may be effected before or after the precipitation. Preferably, two independent inactivations are carried out, e.g., one treatment before the single-step precipitation, and a second treatment thereafter.

In a further preferred embodiment, the protein composition is characterized in that factor XIII is contained. Preferably, factor XIII is admixed, and the factor XIII content is, e.g., at least 80 units per g of fibrinogen, preferably at least 100 U/g of fibrinogen. In case also the fibrin-cross-linking reaction-inhibiting substances, such as, e.g., antibiotics, are present in the preparation, the factor XIII content preferably is increased to at least 500 U/g of fibrinogen. Preferably, factor XIII is admixed as a purified, separately virus-inactivated product (particularly preferably a factor XIII preparation produced according to EP 0 637 451).

In a further preferred embodiment; the protein composition is characterized by a low plasminogen content. The content of plasminogen preferably is 1.6 mg/g of fibrinogen at the most, more preferred less than 0.8 mg/g of fibrinogen, most preferred less than 0.3 mg/g of fibrinogen.

The protein composition according to the invention advantageously comprises fibronectin and fibrinogen at a ratio of from 0.02 to 0.5, preferably from 0.02 to 0.25, also preferred from 0.02 to 0.2, more preferred from 0.04 to 0.16, most preferred around 0.1 (0.05 to 0.15), i.e., in contrast to highly pure fibrinogen preparations (WO 94/20524), it still contains substantial portions of fibronectin.

The protein composition may further comprise active ingredients, such as antibiotics, growth factors, pain alleviating substances or combinations thereof.

In a preferred embodiment, the protein composition according to the invention is characterized in that
  a) as a solution, it contains at least 70 mg of fibrinogen/ml or can be reconstituted or liquefied, respectively, to such a solution,
  b) at 20° C., it has a viscosity of 350 cSt at the most, preferably at an osmolarity of less than 500 mOsm, most preferred of less than 400 mOsm,
  c) after mixing with a thrombin-CaCl$_2$ solution, it forms a non-transparent clot of physiological fibrin structure, and
  d) it does not contain an addition of a solubility-improving substance with a benzene, pyridine, piperidine, pyrimidine, morpholine, pyrrole, imidazole, pyrazole, furan, thiazole or purin-containing group.

In a further preferred embodiment, the protein composition according to the invention is characterized in that
  a) as a solution it contains at least 70 mg of fibrinogen/ml, or can be reconstituted or liquefied, respectively, to such a solution,
  b) at 20° C., it has a viscosity of 150 cSt at the most, preferably at an osmolarity of less than 500 mOsm, most preferred of less than 400 mOsm,
  c) after mixing with a thrombin-CaCl$_2$ solution, it forms a non-transparent clot of physiological fibrin structure, and
  d) it contains one or several solubilizing substances with a benzene, pyridine, piperidine, pyrimidine, morpholine, pyrrole, imidazole, pyrazole, furan, thiazole or purine-containing group at a concentration of a total of 150 mM at the most.

The inventive protein compositions or pharmaceutical preparations, respectively, are versatile in terms of use. In particular, the preparations according to the invention are used for tissue adhesion, haemostasis and/or wound healing.

In a further preferred embodiment, the inventive protein compositions or preparations, respectively, can also be used to produce a fibrin-based biomatrix. To this end, the solution of a protein composition or pharmaceutical preparation, respectively, of the invention is admixed with an enzyme suitable for converting fibrinogen into fibrin, preferably with thrombin, and the fibrin formed is used either in its fresh state or after lyophilisation and re-moistening, as the carrier material for growing cells, or as a so-called biomatrix (cf., e.g., WO 99/15209)

The biomatrix of the invention may be present in various forms, e.g. as a sponge, a film, as micro-beads or as flakes.

The fibrin-based biomatrix is particularly suitable for growing cells, in particular human cells. Keratinocytes, fibroblasts, chondrocytes are to be mentioned as an example of cells capable of being cultured or grown by means of this fibrin matrix. Such a biomatrix is also suitable for dressing wounds or as tissue substitute, respectively, particularly as a skin substitute.

The invention will now be explained in more detail by way of the following examples and the drawing figures, to which, however, it shall not be restricted.

EXAMPLES

Example 1

Human plasma cryoprecipitate prepared according to methods known per se was dissolved with the 4-fold amount of a buffer solution containing 20 mM sodium citrate, 120 mM sodium chloride, 5 mM tranexamic acid as well as 1200 IU heparin/l, the PH was adjusted to 7.3, and it was filtered to clarification. Aliquots of this solution were admixed with solutions containing glycine and polyethylene glycol 4000 (PEG 4000) under stirring at room temperature, so that in each case a final concentration of 1 M glycine, yet different final concentrations of PEG 4000 ranging from 1 to 10% (w/v) were obtained.

DETAILED DESCRIPTION OF THE INVENTION

The precipitates formed were centrifuged off, and the relative content of fibrinogen (Fbg), fibronectin (Fn) and albumin (Alb) was determined by means of SDS-PAGE of the non-reduced and reduced samples, staining with Coomassie Blue and densitometric evaluation (cf. also EP 0 345 246, Examples 1–37).

Figure 1:
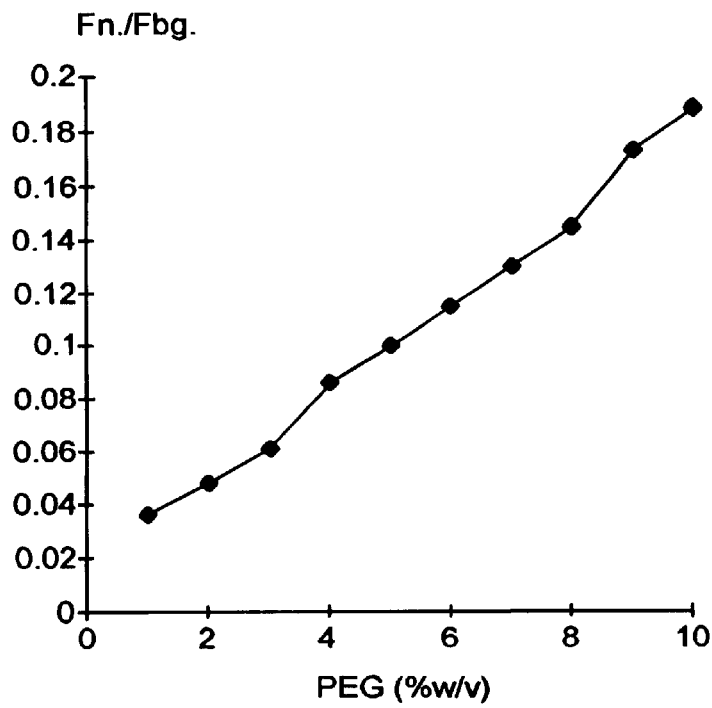
FIG. 1 shows the dependence of the ratio of fibronectin to fibrinogen (Fn/Fbg) in the precipitate on the PEG concentration in the precipitation mixture (glycine concentration: 1 M)

The results have been summarized in Table 1; the ratio of fibronectin: fibrinogen in dependence on the PEG concentration is also graphically represented in FIG. 1.

TABLE 1

Dependence of the protein composition of the precipitate on the PEG content in the precipitation mixture (glycine concentration: 1 M)

| PEG % (w/v) | Fibrinogen % Protein | Fibronectin % Protein | Albumin % Protein | Fibronectin: Fibrinogen |
|---|---|---|---|---|
| 1 | 84 | 3 | 5 | 0.04 |
| 2 | 83 | 4 | 5 | 0.05 |
| 3 | 82 | 5 | 4 | 0.06 |
| 4 | 81 | 7 | 4 | 0.09 |
| 5 | 80 | 8 | 4 | 0.10 |
| 6 | 78 | 9 | 3 | 0.12 |
| 7 | 77 | 10 | 3 | 0.13 |
| 8 | 76 | 11 | 3 | 0.15 |
| 9 | 75 | 13 | 2 | 0.17 |
| 10 | 74 | 14 | 2 | 0.19 |

The Example shows how protein precipitates can be obtained according to the invention from a plasma protein mixture by a single precipitation with a mixture of two components (here, glycine and PEG), which protein precipitates contain variable amounts of fibronectin in addition to the main component fibrinogen, wherein the ratio fibronectin: fibrinogen can be adjusted as desired within certain limits (e.g. by selection of the agents according to Example 1 in a range of between 0.02–0.2) by a suitable choice of the concentrations of the agents and their ratio to each other, respectively. Such protein precipitates are, e.g., suitable for producing fibrinogen-based tissue adhesives (fibrin adhesives).

Example 2

Human plasma cryoprecipitate was dissolved analogous to Example 1, the pH was adjusted to 7.3, and it was filtered to clarification. Aliquots of this solution were admixed analogous to Example 1 with solutions containing glycine and PEG 4000, so that in each case a final PEG concentration of 6.5% (w/v), yet various glycine concentrations ranging from 0.2 to 1 M were obtained. The precipitates formed were centrifuged off analogous to Example 1 and analyzed.

Figure 2:
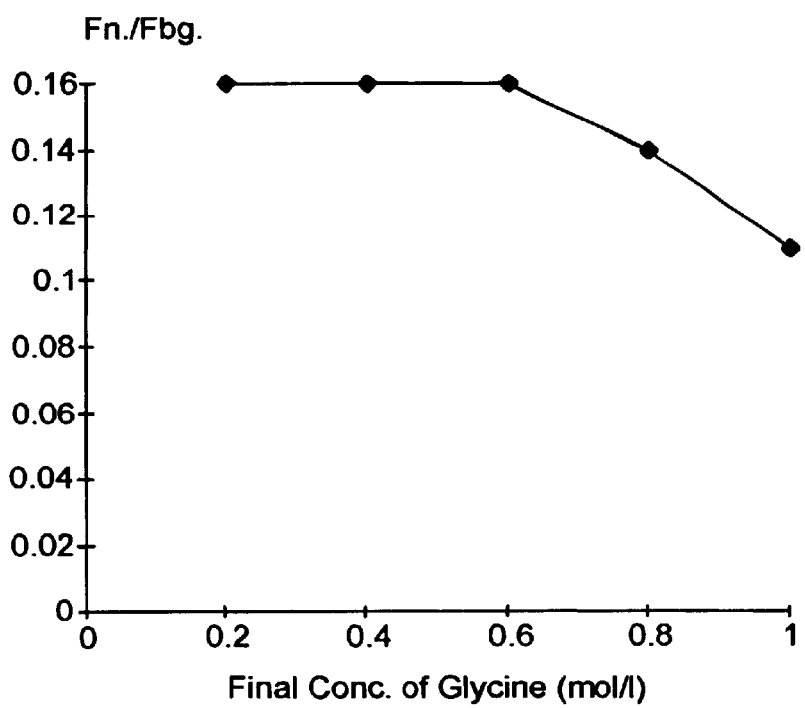
FIG. 2 shows the dependence of the ratio of fibronectin to fibrinogen (Pn/Fbg) in the precipitate on the glycine concentration in the precipitation mixture (PEG concentration: 6.5% w/v)

In all variants, the protein yield was approximately 95%. The ratio fibronectin: fibrinogen in dependence on the glycine concentration has been summarized in Table 2 and is additionally graphically represented in FIG. 2.

TABLE 2

Dependence of the protein composition of the precipitate on the glycine content in the precipitation mixture (PEG concentration: 6.5% w/v).

| Glycine mol/l | Fibronectin: Fibrinogen |
|---|---|
| 0.2 | 0.16 |
| 0.4 | 0.16 |
| 0.6 | 0.16 |
| 0.8 | 0.14 |
| 1.0 | 0.11 |

Supplementing Example 1, this Example illustrates that protein precipitating agents known per se, such as glycine, by no means merely act as precipitating agents when used in combination with PEG, but that under certain conditions glycine, e.g., may also act as a solubilizer for fibronectin, this being in a range of conentration in which hitherto glycine was merely known as a protein-precipitating agent.

The following Examples 3–5 show comparable compositions of preparations obtained according to the prior art.

Example 3

A plasma cryoprecipitate was dissolved as in Example 1. While stirring at room temperature, glycine was added up to a final concentration of 2 mol/l. The protein precipitate formed was centrifuged off and analyzed as in Example 1. Fibrinogen was almost completely precipitated. The relative content of fibrinogen amounted to 86% of the total protein, the relative content of fibronectin was 1.5%. The ratio fibronectin: fibrinogen thus was 0.017.

Example 4

A plasma cryoprecipitate was dissolved as in Example 1. While stirring at room temperature, PEG 4000 was added up to a final concentration of 10% (w/v). The protein precipitate formed was centrifuged off and analyzed as in Example 1. Fibrinogen was almost completely precipitated. The relative content of fibrinogen amounted to 72% of the total protein, the relative content of fibronectin was 16%. The ratio fibronectin fibrinogen thus was 0.22.

Example 5

A plasma cryoprecipitate was dissolved as in Example 1. While stirring at room temperature, PEG 4000 was added up to a final concentration of 10% (w/v). The protein precipitate formed was centrifuged off, dissolved again, and glycine was added to the solution to a final concentration of 2 M, under stirring at room temperature. The protein precipitate formed was centrifuged off again and analyzed as in Example 1. The relative content of fibrinogen amounted to 93% of the total protein, the relative content of fibronectin was 1.5%. The ratio fibronectin: fibrinogen thus was 0.016.

Examples 3–5 show that with the methods known in the prior art it is not possible to arrive, in one or also in several consecutive steps, at protein mixtures having a defined ratio of fibronectin: fibrinogen, e.g., when using a combination of glycine and PEG in the concentrations used in Example 1 or 2, to arrive at a ratio in the range of from 0.02 to 0.2.

Example 6

Production of a lyophilized preparation according to the invention, with two independent virus inactivation steps:

Human plasma cryoprecipitate prepared according to methods known per se was dissolved with the 4-fold amount of a buffer solution (LP1) containing 20 mM sodium citrate, 120 mM sodium chloride, 5 mM tranexamic acid (t-AMCHA) as well as 1200 IU heparin/l, and was filtered to clarification. Subsequently, a so-called solvent-detergent (SD) treatment was carried out to inactivate enveloped viruses possibly present. To this end, a mixture of Triton X-100, Tween 80 (Polysorbat-80K) and tri-n-butylphosphate (TNBP) was admixed to give final concentrations of 1%, 0.3% and 0.3% (v/v), respectively. After stirring for 1 h at RT, it was again filtered to clarification. The solution was admixed with the equal volume of a solution containing 2 M glycine and 13% (w/v) PEG 4000 (precipitating composition) under stirring at room temperature, stirred for 30 min and centrifuged. The sediment was comminuted and again dissolved in LP1 containing 1% Tween 80, and the precipitation was repeated in the same manner. To remove the SD and precipitating reagents, the sediment was then comminuted and treated in the cold (0–2° C.) 2×with the 10-fold amount of a buffer solution containing 10 mM $Na_3$ citrate and 5 mM t-AMCHA in the presence of small amounts of Tween 80. The washed sediment was then dissolved in a buffer solution containing 10 mM $Na_3$ citrate and 5 mM t-AMCHA. After adjusting the protein concentration to 40 g/l, the solution was lyophilzed as a whole. For further virus inactivation, the lyophilized material was adjusted to a residual moisture of 7–8% and heated for 10 h at 60° C. +1 h at 80° C. under the exclusion of oxygen. The thus-treated lyophilisate was dissolved in 20 mM niacinamide solution to a protein concentration of 38 g/l, admixed with 6 g of pasteurized human albumin/l, and the pH was adjusted to 7.3.

The solution was sterile-filtered, filled at 5.0 ml each into final containers (small glass bottles) under sterile conditions and lyophilized.

The final product thus obtained gave a ready-to-use solution when dissolved with 2.0 ml of water for injection (WFI), or with 2.0 ml of 50 mM t-AMCHA solution, having a fibrinogen content of more than 70 mg/ml. This solution may, e.g., be used as a tissue adhesive.

In principle, instead of using pure water, the lyophilized final product may also be dissolved with aqueous solutions containing additional active substances, such as, e.g., fibrinolysis inhibitors, coagulation factor XIII, antibiotics, growth factors, pain-alleviating substances etc.

The product produced according to the above-described method in its protein content and composition substantially corresponded to the tissue adhesive preparation described in EP 804933A2 (Example 2) The fibronectin: fibrinogen ratio was approximately 0.09, the plasminogen content merely about 0.15 mg/g of fibrinogen. After mixing the ready-to-use tissue adhesive solution with the equal volume of a thrombin-$CaCl_2$ solution, physiological, non-transparent, visco-elastic clots were formed.

Despite this broad agreement with the product described in EP 804933, the tissue adhesive according to the invention is characterized by a markedly reduced viscosity, with an identical content of a substance improving the solubility of fibrinogen (50 mM niacinamide).

This is the more surprising as the preparation according to the invention had not only been subjected to one, but had been subjected to two independent virus inactivation steps and, moreover, the vapor treatment had been carried out under aggravated conditions (10 hours, 60° C., +1 hour, 80° C.). According to experience, such a heat treatment leads to a poorer solubility and an increased viscosity.

Therebeyond, surprisingly it has been found that t-AMCHA, in addition to its known antifibrinolytic effect, lowers the viscosity of fibrinogen-containing solutions. In particular, the viscosity of the tissue adhesive solutions obtained according to the invention is further lowered by t-AMCHA (cf. Table 3).

TABLE 3

| | Viscosity [cSt] in the presence of 50 mM niacinamide | | |
| --- | --- | --- | --- |
| Temperature [° C.] | Tissue adhesive acc. to invention | Tissue adhesive acc. to invention + 50 mM t-AMCHA | Tissue adhesive according to EP 804933A2 (Example 2) |
| 20 | 99 | 78 | 277 |
| 25 | 76 | 63 | 132 |
| 30 | 56 | 52 | 81 |
| 37 | 39 | 34 | 53 |

Example 7

Production of a liquid deep-frozen tissue adhesive according to the invention with two independent virus inactivation steps:

Up to sterile filtration, the production was carried out analogous to Example 6. Subsequently, the sterile-filtered solution was lyophilized under sterile conditions once more, dissolved to a concentrated tissue adhesive solution, filled into final containers. (disposable syringes) and stored in the deep-frozen state. Prior to use, such a preparation need only be thawed.

The ready-to-use tissue adhesive solution had the same properties as the dissolved preparation of Example 6.

Instead of lyophilizing again the sterile filtered, diluted tissue adhesive solution and to dissolve it in concentrated state, it may also be evaporated directly under mild vacuum to a concentrated tissue adhesive solution.

Methodology of Viscosity Measurement

To standardize the measurement method, a sample of the tissue adhesive solution initially is frozen at $\leq -20°$ C. To determine its viscosity, the sample is thawed in a water bath at the desired measurement temperature, incubated for approximately 30 min at this temperature and then its viscosity is determined in a temperature-controlled capillary viscosimeter. Subsequently, the sample can be incubated at a higher temperature in the viscosimeter, and the measurement may be repeated at that temperature. The individual measurements are effected in series at rising temperatures. If measured in the reverse sequence, falsified values (too low) could be obtained, since the equilibrium is reached only slowly at decreasing temperatures.

Example 8

Figure 3:
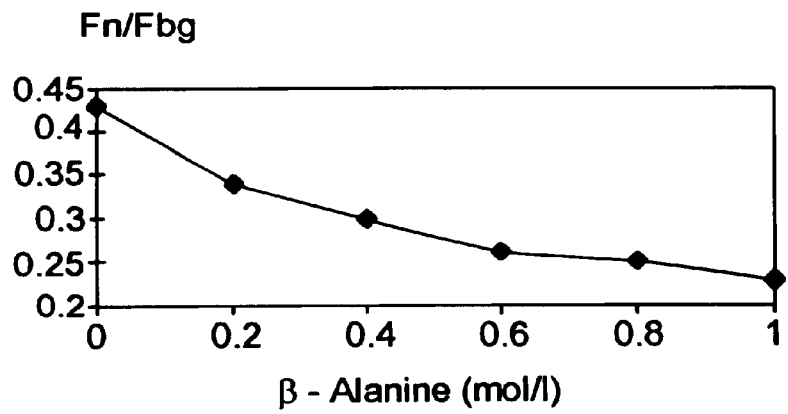
FIG. 3 shows the dependence of the ratio of fibronectin to fibrinogen (Fn/Pbg) in the precipitate on the β-alanine concentration in the precipitation mixture (ethanol concentration: 2% v/v)

A plasma cryoprecipitate was dissolved as in Example 1, the pH was adjusted to 7.3, and it was filtered to clarification. Analogous to Example 1, aliquots of this solution were admixed with solutions containing β-alanine and ethanol, yet not at RT, but at 0° C., so that in each case an ethanol concentration of 2% (v/v), yet different β-alanine concentrations ranging from 0–1 M were obtained. The precipitates formed were centrifuged off analogous to Example 1 and analyzed. In FIG. 3, the ratio Fn/Fbg in dependence on the β-alanin concentration is graphically represented.

TABLE 4

Dependence of the protein composition of the precipitate on the β-alanine content in the precipitation mixture (ethanol concentration: 2%)

| β-Alanine [M] | Fn/Fbg |
|---|---|
| 0.0 | 0.43 |
| 0.2 | 0.34 |
| 0.4 | 0.30 |
| 0.6 | 0.26 |
| 0.8 | 0.25 |
| 1.0 | 0.23 |

Analogous to Example 2, this Example shows that protein precipitating agents known per se, such as β-alanine, when used in combination with ethanol, by no means merely act as a precipitating agent, but that under certain conditions β-alanine, e.g., may also act as a solubilizer for fibronectin.

The following Examples 9–11 show comparable compositions of preparations obtained according to the prior art.

Example 9

A plasma cryoprecipitate was dissolved as in Example 1. Under stirring at 0° C., β-alanine was added up to a final concentration of 2 M. The protein precipitate formed was centrifuged off and analyzed as in Example 1. The relative content of fibrinogen amounted to 74% of the total protein, the relative content of fibronectin to 16%. The ratio Fn/Fbg thus was 0.22.

Example 10

A plasma cryoprecipitate was dissolved as in Example 1. Under stirring at 0° C., ethanol was added up to a final concentration of 2% (v/v). The protein precipitate formed was centrifuged off and analyzed as in Example 1. The relative content of fibrinogen amounted to 67% of the total protein, the relative content of fibronectin to 29%. The ratio Fn/Fbg thus was 0.43.

Example 11

A plasma cryoprecipitate was dissolved as in Example 1. Under stirring at 0° C., ethanol was added up to a final concentration of 2% (v/v). The protein precipitate formed was centrifuged off, dissolved again, and β-alanine was added to the solution under stirring at 0° C. up to a final concentration of 2 M. The protein precipitate formed was centrifuged off again, and analyzed as in Example 1. The relative content of fibrinogen amounted to 77% of the total protein, the relative content of fibronectin to 16%. The ratio Fn/Fbg thus was 0.21.

Examples 9–11 show that with the methods known in the prior art it is not possible, in one or also in several consecutive steps, to arrive at protein mixtures having defined ratios of Fn/Fbg, e.g. when using a combination of β-alanine and ethanol at the concentrations used in Example 8, to arrive at a ratio ranging from 0.23–0.34.

Example 12

Figure 4:
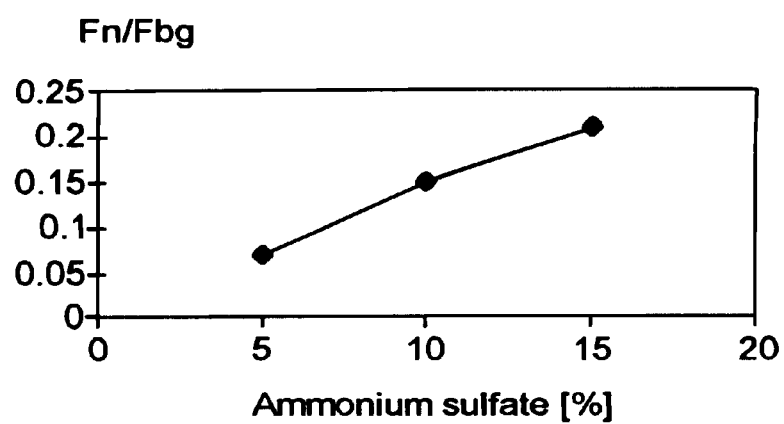
FIG. 4 shows the dependence of the ratio of fibronectin to fibrinogen (Fn/Fbg) in the precipitate on the ammonium sulfate concentration in the precipitation mixture (β-alanine concentration: 1M)

A plasma cryoprecipitate was dissolved as in Example 1, the pH was adjusted to 7.3, and it was filtered to clarification. Analogous to Example 1, aliquots of this solution were admixed with solutions containing β-alanine and ammonium sulfate, so that in each case a β-alanine concentration of 1 M, yet different ammonium sulfate concentrations ranging form 5–15W (w/v) were obtained, The precipitates formed were centrifuged off analogous to Example 1 and analyzed. The results have been summarized in Table 5; in FIG. 4, the ratio En/Fbg in dependence on the ammonium sulfate concentration is graphically represented.

TABLE 5

Dependence of the protein composition of the precipitate on the ammonium sulfate content in the precipitation mixture (β-alanine concentration: 1 M)

| Ammonium sulfate % (w/v) | Fbg (% Prot.) | Fn (% Prot.) | Alb (% Prot.) | Fn/Fbg |
|---|---|---|---|---|
| 5 | 69 | 5 | 0 | 0.07 |
| 10 | 78 | 12 | 0 | 0.15 |
| 15 | 78 | 16 | 0 | 0.21 |

Similar to Example 1, this Example shows how protein precipitates can be obtained from a plasma protein mixture by a single precipitation with a precipitating composition comprising two components (here, β-alanine and ammonium sulfate), which protein precipitates contain variable amounts of fibronectin, wherein the ratio Fn/Fbg can be adjusted as desired within certain limits (e.g. by selection of the components according to Example 12 in a range of between 0.07 and 0.21) by a suitable choice of the concentrations of the components and their ratio to each other, respectively.

Example 13

Figure 5:
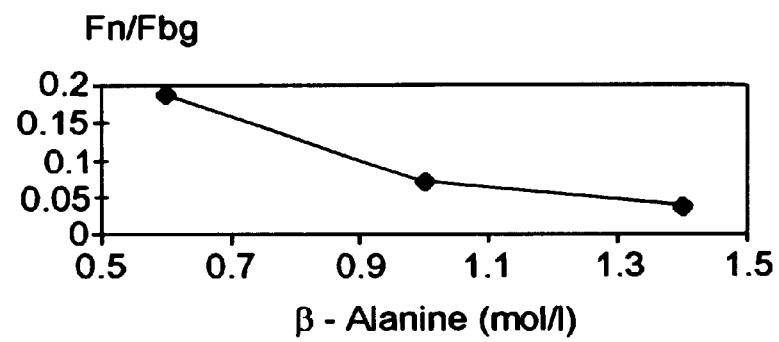
FIG. 5 shows the dependence of the ratio of fibronectin to fibrinogen (Fn/Fbg) in the precipitate on the β-alanine concentration in the precipitation mixture (ammonium sulfate concentration: 5% w/v)

A plasma cryoprecipitate was dissolved as in Example 1, the pH was adjusted to 7.3, and it was filtered to clarification. Analogous to Example 1, aliquots of this solution were admixed with solutions containing β-alanine and ammonium sulfate, so that in each case an ammonium sulfate concentration of 5% (w/v), yet different β-alanine concentrations ranging from 0.6–1.4 M were obtained. The precipitates formed were centrifuged off analogous to Example 1 and analyzed. In FIG. 5, the ratio Fn/Fbg in dependence on the β-alanine concentration is graphically represented.

TABLE 6

Dependence of the protein composition of the precipitate on the
β-Ala content in the precipitation mixture (ammonium sulfate
concentration: 5%)

| β-Alanine [M] | Fn/Fbg |
|---|---|
| 0.6 | 0.19 |
| 1.0 | 0.07 |
| 1.4 | 0.04 |

Analogous to Example 2, this Example shows that protein precipitating agents known per se, such as β-alanine, when used in combination with ammonium sulfate by no means merely act as precipitating agents, but that under certain conditions β-alanine, e.g., may also act as a solubilizer for fibronectin.

The following Examples 14–16 show comparable compositions of preparations obtained according to the prior art.

Example 14

A plasma cryoprecipitate was dissolved as in Example 1. Under stirring at RT, β-alanine was added up to a final concentration of 2 M. The protein precipitate formed was centrifuged off and analyzed as in Example 1. The relative content of fibrinogen amounted to 82% of the total protein, the relative content of fibronectin to 1%. The ratio Fn/Fbg thus was 0.01.

Example 15

A plasma cryoprecipitate was dissolved as in Example 1. Under stirring at RT, ammonium sulfate was added up to a final concentration of 15% (w/v). The protein precipitate formed was centrifuged off and analyzed as in Example 1. The relative content of fibrinogen amounted to 76% of the total protein, the relative content of fibronectin to 16%. The ratio Fn/Fbg thus was 0.21.

Example 16

A plasma cryoprecipitate was dissolved as in Example 1. Under stirring at RT, ammonium sulfate was added up to an ammonium sulfate concentration of 5% (w/v). The protein precipitate formed was centrifuged off, dissolved again, and β-alanine was added to the solution under stirring at RT up to a final concentration of 2 M. The protein precipitate formed was centrifuged off again and analyzed as in Example 1. The relative content of fibrinogen amounted to 84% of the total protein, the relative content of fibronectin to 1%. The ratio Fn/Fbg thus was 0.01.

Examples 14–16 show that with the methods known in the prior art it is not possible, in one or also in several consecutive steps, to arrive at protein mixtures having a defined ratio of Fn/Fbg, e.g. when using a combination of β-alanine and ammonium sulfate at the concentrations used in Example 13, to arrive at a ratio ranging from 0.04–0.19.

What is claimed is:

1. A method for producing a pharmaceutical preparation comprising fibronectin and fibrinogen, said method comprising the steps of:
    (a) providing a fibrinogen and fibronectin-containing starting solution;
    (b) admixing to the starting solution at room temperature, in a single step, a precipitating composition comprising a polyalkylene glycol and at least one amino acid selected from the group consisting of glycine and β-alanine, to form a precipitate;
    (c) collecting said precipitate containing fibronectin and fibrinogen; and
    (d) preparing said pharmaceutical preparation from said precipitate, wherein the pharmaceutical preparation has a fibronectin: fibrinogen ratio from 0.02 to 0.2.

2. The method of claim 1 wherein the polyalkylene glycol is polyethylene glycol admixed to the starting solution to a final concentration of from 1 to 12% w/v, and the amino acid is glycine admixed to the starting solution to a final concentration of from 0.2 to 3.0 M.

3. The method of claim 1 wherein the starting solution is derived from cryoprecipitate.

4. The method of claim 1 wherein the precipitating composition is admixed in liquid form.

5. The method of claim 1, wherein the starting solution is checked for the absence of pathogens.

6. The method of claim 1 further comprising a step for inactivating or depleting pathogens which is carried out before or after the step (b).

7. The method of claim 6 wherein said step for inactivating or depleting pathogens is a treatment selected from the group consisting of heat, solvent, detergent, and combinations thereof.

8. The method of claim 6 wherein the step for inactivating or depleting pathogens is filtration.

9. The method of claim 8 wherein the filtration is ultrafiltration.

10. The method of claim 8 wherein the filtration is conducted in the presence of virus-binding agents.

11. The method of claim 1, wherein, after step (d), at least one ingredient is admixed into the pharmaceutical preparation, said ingredient being selected from the group consisting of fibrinolysis inhibitors, factor XIII, antibiotics, growth factors, pain-alleviating substances, and anti-inflammatory agents.

12. The method of claim 1, wherein said pharmaceutical preparation is a deep-frozen or lyophilized precipitate.

13. The method of claim 1, wherein said pharmaceutical preparation is a solution comprising at least 70 mg/ml fibrinogen.

14. The method of claim 1, further comprising the steps of dissolving the precipitate of step (c) and repeating steps (b) and (c) at least once.

15. The method of claim 1, wherein the pharmaceutical preparation is a solution that has a viscosity below 150 cSt at 20° C., an osmolarity below 400 mOsm, and wherein the pharmaceutical preparation, after mixing with a thrombin $CaCl_2$ solution, forms a non-transparent clot of physiological fibrin suture.

16. The method of claim 1, wherein the pharmaceutical preparation is a solution that has a viscosity of 99 cSt at 20° C., an osmolarity below 400 mOsm, and wherein the pharmaceutical preparation, after mixing with a thrombin $CaCl_2$ solution, forms a non-transparent clot of physiological fibrin structure.

17. A method for producing a pharmaceutical preparation comprising fibronectin and fibrinogen, the method comprising the steps of:
    (a) providing a fibrinogen and fibronectin-containing starting solution;
    (b) admixing to the starting solution at room temperature, in a single step, a precipitating composition comprising a polyalkylene glycol and at least one amino acid selected from the group consisting of glycine and β-alanine, to form a precipitate;
    (c) collecting said precipitate containing fibronectin and fibrinogen; and (d) preparing said pharmaceutical preparation from said precipitate, wherein the pharmaceutical preparation is a solution or a reconstituted solution that has a fibronectin: fibrinogen ration from 0.02 to 0.2, a fibrinogen concentration of at least 70 mg/ml, a viscosity of 99 cSt at 20° C., an osmolarity below 400 mOsm, and wherein the pharmaceutical preparation, after mixing with a thrombin $CaCl_2$ solution, forms a non-transparent clot of physiological fibrin structure.

18. The method of claim 17, further comprising the steps of dissolving the precipitate of step (c) and repeating steps (b) and (c) at least once.

* * * * *